(12) United States Patent
Huyberechts et al.

(10) Patent No.: US 6,330,465 B1
(45) Date of Patent: Dec. 11, 2001

(54) GASTRO-INTESTINAL PROBE

(75) Inventors: Guido Huyberechts, Melsbroeck; Gaston Vantrappen, 142 Meerlaan, B-3090 Overijse, both of (BE)

(73) Assignees: Imec vzw, Leuven; Gaston Vantrappen, Overijse, both of (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/206,268

(22) Filed: Dec. 4, 1998

Related U.S. Application Data

(63) Continuation of application No. 08/451,251, filed on May 26, 1995, now Pat. No. 6,006,121.

(51) Int. Cl.$^7$ ...................................... A61B 5/00
(52) U.S. Cl. ........................ 600/343; 600/350; 600/380
(58) Field of Search ................................ 600/117, 309, 600/340, 343, 350, 380, 341, 342, 348, 373; 607/133; 150/227.11, 227.14, 231.1

(56) References Cited

U.S. PATENT DOCUMENTS

| | | | |
|---|---|---|---|
| 4,710,623 | * 12/1987 | Lipson et al. | 250/227.11 |
| 5,015,843 | * 5/1991 | Seitz et al. | |
| 6,006,121 | * 12/1999 | Vantrappen et al. | 600/343 |

* cited by examiner

*Primary Examiner*—Roy Gibson
(74) *Attorney, Agent, or Firm*—Knobbe, Martens, Olson and Bear, LLP

(57) ABSTRACT

Gastrointestinal probe (2) comprising a sensitive material (4) which is able to be connected to electrical or optical readout means or measurement means (10) characterized in that said sensitive material (4) undergoes an irreversible change when it is submitted to the cumulative action of the external medium, in such a manner that the irreversible change can be measured and/or recorded by said electrical or optical readout means or measurement means (10).

The present invention concerns also the production process of the gastrointestinal probe according to the invention and its use.

17 Claims, 5 Drawing Sheets

GASTRO-INTESTINAL PROBE

This is a continuation of application Ser. No. 08/452,251 filed May 26, 1995 now U.S. Pat. No. 6,006,121.

FIELD OF THE INVENTION

The present invention concerns a gastrointestinal probe intended for the measure of the aggressive force and deleterious effects that gastrointestinal secretions or biliopancreatic secretions and other gastrointestinal contents or forces may exert on the mucosa and surrounding tissues of oesophagus, stomach and intestines.

BACKGROUND OF THE INVENTION

The gastrointestinal tract comprises a mucosal surface which is submitted to aggressive secretions and/or body forces involved in the digestion. In the stomach, the digestion is obtained by the secretion of the acid gastric juice. Presently available methods to evaluate in man the aggressive and damaging powers of digestive secretions are based on intraluminal pH measurements or on biochemical assays. Intraluminal pH measurements yield an instantaneous measure of the acidity of the gastrointestinal contents at a given location in the gastrointestinal tract. Biochemical assays measure in vitro parameters such as enzyme activities in an amount of digestive juices collected over a given period of time. These approaches only allow to measure instantaneous changes in parameters which are known or assumed to have a role in the production of tissue damages.

Examples of intraluminal pH-sensing electrodes are glass or plastic electrodes, ISFET (Ion Sensitive Field Effect Transistor) optical electrodes, combination electrodes or unipolar monocrystalline antimony electrodes (connected to a pH-meter via a cable).

The reference "Chemical Sensors based on Fiber Optics", Analytical Chemistry 56(1), 16A–34A, W. R. Seitz, Easton U.S. (1984) describes devices involving a reagent phase on the end of an optic fiber. In operation, interaction with analytes leads to a change in optical properties of the reagent phase, which is probed and conducted through the optic fiber.

In particular, a class of irreversible sensors is described. The "irreversible" sensing principle, in the sense of a reagent consuming system, is based on analytical reactions that consume reagent. Said "irreversible" sensors can have a lifetime of months, or years but act within said lifetime as reversible systems with respect to sensor response. Said reversibility means that whenever said "irreversible" sensor is transferred from a first medium, e.g. with oxygen partial pressure (a), to a second medium with oxygen partial pressure(b), and thereafter back to said first medium, said sensor back in the first medium will again record an oxygen partial pressure.

The document "Research on Gastric Multiparameter Sensors Technology", Proceedings of ICEE Engineering in Medicine and Biology Society, vol. 14, 16–120, X. Lin et al. (1992) introduces gastric multiparameter sensor technology and describes devices based on reversible measurement principle.

Problem Definition

Above-mentioned electrodes based upon an instantaneous and reversible measure of the intraluminal pH do not give a correct measure of the aggressive action due to the secretions and the body forces in the gastrointestinal tract.

Furthermore, the effects of other physical and biochemical factors such as enzymatic catalysis by pepsin, trypsin and other enzymes, bile secretions, osmotic forces, pressure or flow of intestinal contents, are not measured by these electrodes.

Methods to measure the irreversible and cumulative changes produced by prolonged contact with digestive secretions are not available. Such measurements should give a more direct and more accurate estimate of the expected tissue damage in several disease entities. This information is much needed because it should shed new light on pathological aspects of various diseases such as acid-peptic diseases (reflux oesophagitis, peptic ulcer, gastritis, duodenitis, Zollinger Ellison syndrome) and diseases where other enzymatic activities, such as tryptic activity, may play a role (coeliac disease, inflammatory bowel disease). As presently available methods do not allow to obtain this much needed information, the present invention is developing a gastrointestinal probe which allows one to measure the irreversible and cumulative changes produced upon a substrate in the digestive tract (acidity enzyme activity and other physico-chemical forces).

Aims of the Invention

The main aim of the present invention is to obtain a gastrointestinal probe which may measure by an irreversible change of the sensitive material the effect of the cumulative aggressive force that digestive secretions and other body forces may exert upon the mucosa and surrounding tissues of the digestive tract.

DESCRIPTION OF THE INVENTION

The present invention concerns a gastrointestinal probe comprising a sensitive material which is able to be connected to electrical or optical readout means or measurement means, wherein said sensitive material undergoes an irreversible change when it is submitted to the cumulative action of the external medium, in such a manner that the irreversible change can be measured and/or recorded by said electrical or optical readout or measurement means.

The term "irreversible change of the sensitive material" means a physical or chemical irreversible modification of said material.

The "cumulative action of the external medium" means the cumulative aggressive forces (physical and biochemical force due to enzymatic catalysis, pH modification, bilious secretion, osmotic force, pressure or flow of intestinal content) that gastrointestinal secretions and biliopancreatic secretions and other gastrointestinal contents or forces may exert on the mucosa and surrounding tissues of the gastrointestinal tract (oesophagus, stomach and intestine).

According to the invention, said irreversible change of the said sensitive material is a chemical or physical modification of said sensitive material selected from the group consisting of swelling, hydrolysis, molecular modifications (preferably due to absorption of one or more elements from the external medium), loss, release, decomposition, modification of refractive index, light absorption or any other property of said sensitive material which may be measured or recorded by electrical or optical devices.

Advantageously, the said sensitive material is part of a matrix composed of one or more electrically conducting composite material (s).

Preferably, said matrix comprises:
  a polymeric sensitive material showing characteristics of
    an irreversible change when placed in the area of the digestive tract under examination and exposed to the prolonged action of aggressive secretions and/or body forces involved in the digestion.

an electrically conducting material, preferably evenly dispersed in the polymeric material, in order to create a conductive path which allows the electrical monitoring of the irreversible change of the matrix, possibly, a surrounding protective layer having a retarding effect on the irreversible change of the matrix.

Said polymeric sensitive material is selected from the group consisting of pyridine, styrene, methacrylate based polymers and copolymers, acid resistant polymers, polymeric compositions used as drug coating for pH dependant delivery of active compounds and/or a mixture thereof.

Said electrically conductive material is preferably chosen among the group consisting of metals, semi-conducting oxides, carbon, electronically conducting polymers and/or a mixture thereof.

The present invention concerns also the catheter which comprises the gastrointestinal probe according to the invention, and possibly the electrical or optical readout measurements or devices for measurement.

The form and the size of the gastrointestinal probe and its catheter can differ according to the specific application or introduction pathways into the gastrointestinal tract.

It is another object of the present invention to disclose a production process of the gastrointestinal probe according to the invention wherein the connections between the sensitive material and the electrical or optical readout measurement or devices for measurement are obtained by micro-electronic patterning techniques.

According to a preferred embodiment of the invention, said micro-electronic patterning techniques comprise the following steps: photolithographic patterning a substrate followed by evaporation, sputtering, plating or deposition, using conventional physical or chemical techniques, of a metallic conductor pattern and insulation layers and deposition of a sensitive material upon at least one portion of said photolithographic patterning substrate.

According to another preferred embodiment of the invention, said micro-electronic patterning techniques comprise the following steps: screen printing of metallic conductor and insulator patterns on an inert substrate, preferably chosen among the group consisting of alumina, oxidized silicon, flexible polymer substrates and/or a mixture thereof and deposition of a sensitive material upon at least one portion of said substrate.

Preferably, several compounds are added to the sensitive material in order to facilitate the deposition of said material upon its substrate.

Other deposition steps such as moulding may also require additives well known by a person skilled in the art.

Another object of the present invention concerns the use of the gastrointestinal probe according to the invention for the measure of the aggressive forces produced by secretions and/or body forces involved with the digestion in the gastrointestinal tract.

According to one preferred embodiment, such probes can be used as a NON-continuous measurement device. In this case, the probe is introduced in the patient's gastrointestinal tract and removed the next day for instance. Then the measure is achieved by means of external electronical or optical devices to determine the degree or severity of the aggression. Thus, the electronical or optical devices are not introduced into the patient's gastrointestinal tract.

According to another preferred embodiment, the probe of the invention can be used as a continuous measurement device.

Preferably, the gastrointestinal probe according to the invention is used in the stomach, in the oesophagus, and in the small or large intestine.

BRIEF DESCRIPTION OF THE DRAWINGS

The FIG. 1 represents a schematic view of a catheter comprising a gastrointestinal probe according to the invention.

The FIG. 2 represents the sensor response (S.R.), shown as a relative change in conductivity of the probe before and after 42 minutes immersion period in solutions of the indicated pH.

The FIG. 3 represents the sensor response (SR.) vs. immersion time.

a) the difference for different pH values (increase in slope for lower pH, i.e. higher decomposition rate).

b) the difference with respect to the reversibility of the sensor response as compared to pH electrodes known in the state of the art.

The FIG. 4 represents the representation of the working principle of the probe. Each picture gives the image of a prototype sensor of a possible embodiment after immersion of 42 minutes in solutions of different pH values. All sensors have initial dimensions similar to sensor near pH=5, which remains unaffected in immersion. The decrease in size is clearly visible, resulting in a change in conductivity and clearly indicating the non-reversibility of the sensor operating principle and the disposable nature.

Figure 5:
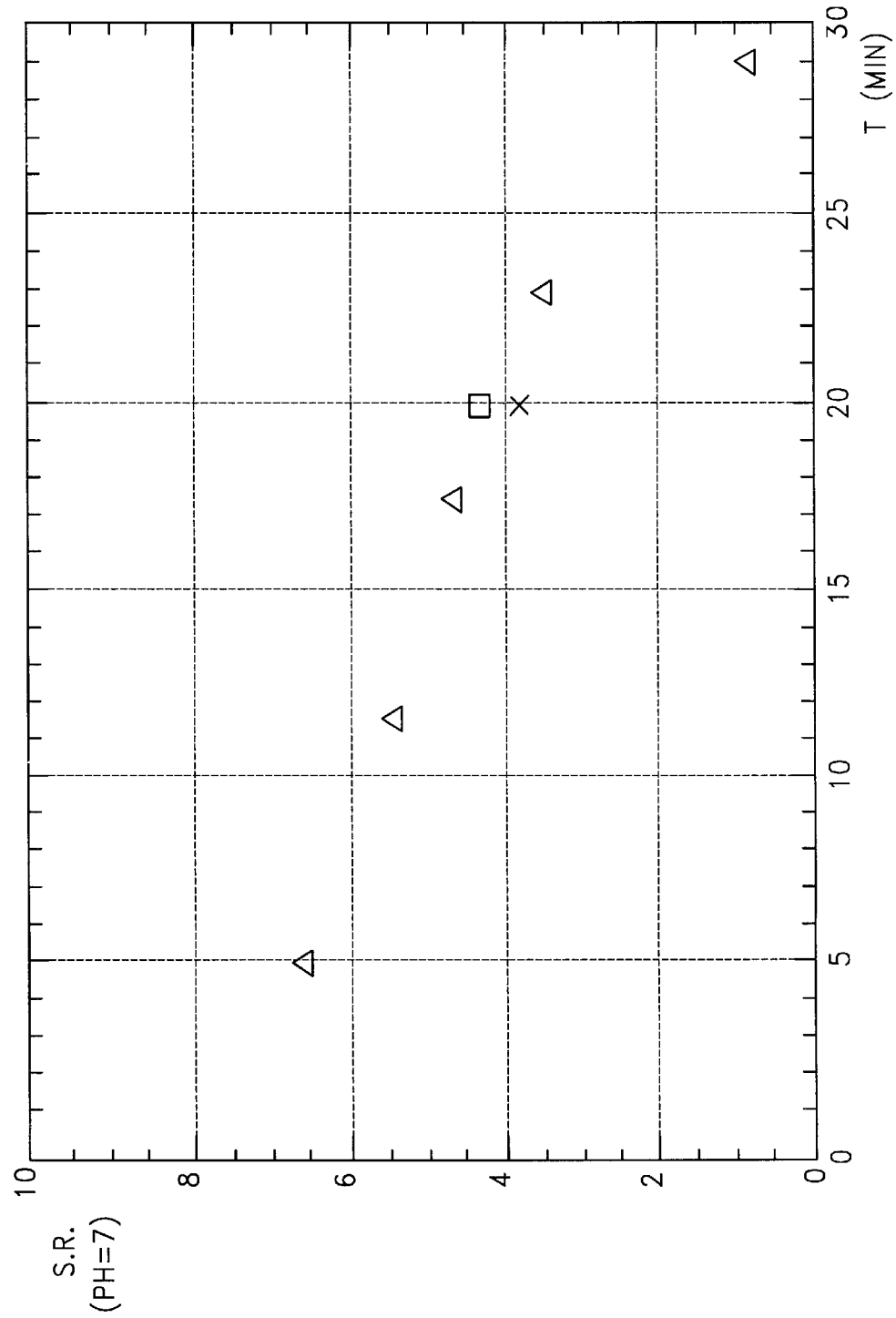

The FIG. 5 represents a sensor response (S.R.) under different immersion conditions, showing the cumulative nature of the response. The results for continuous immersion periods of 20 minutes in pH 2 (X, ■) are compared with the cumulative result after several immersions of approximate 6 minutes periods at pH 2 separated by periods of approximate 6 minutes immersion in non-aggressive media.

Figure 6:
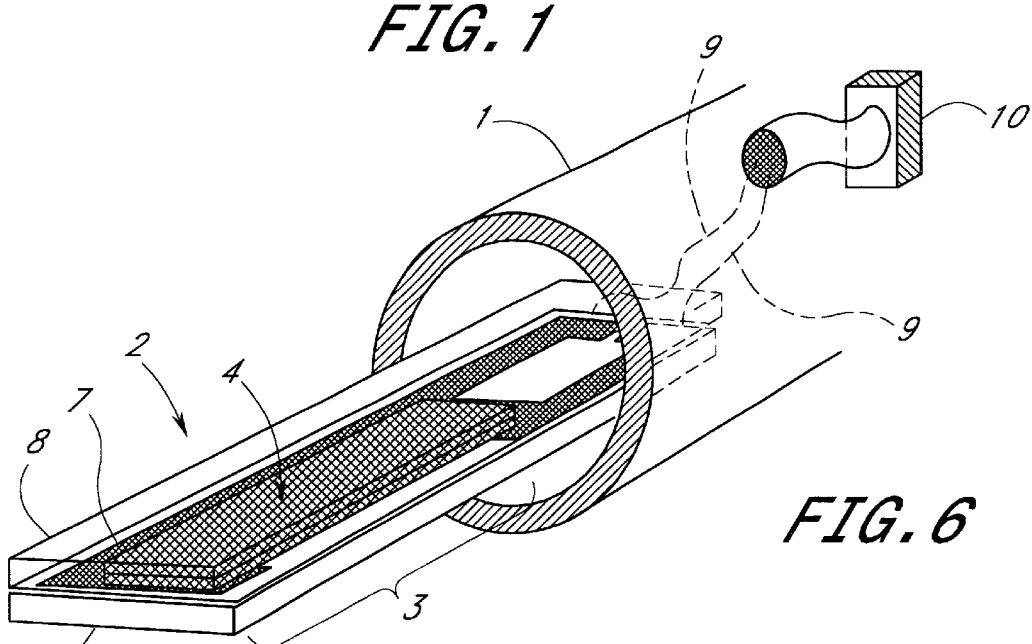

The FIG. 6 represents a schematic view of a catheter comprising a gastrointestinal probe according to another preferred embodiment of the invention.

Figure 7:
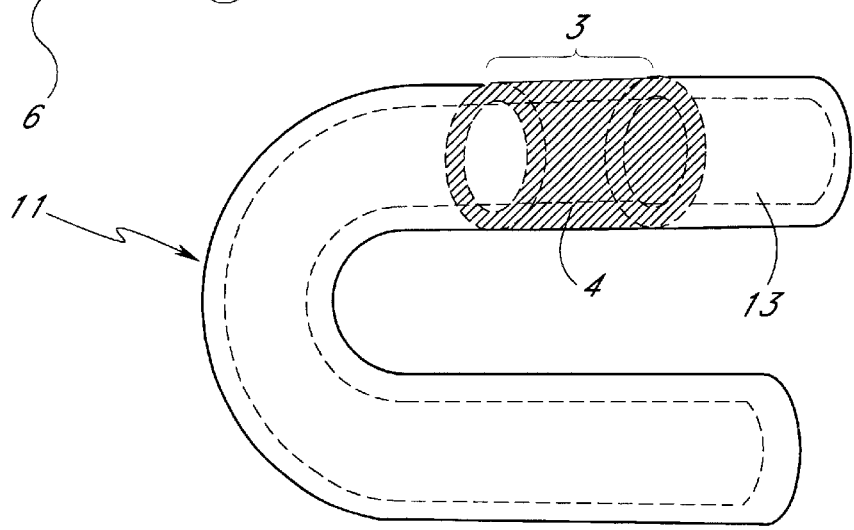

The FIG. 7 represents a schematic view of a gastrointestinal probe according to the invention combined with optical fibres.

DESCRIPTION OF A PREFERRED EMBODIMENT OF THE INVENTION

Figure 1:
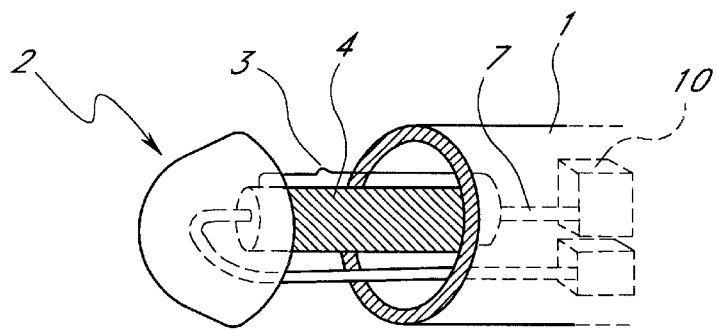

The FIG. 1 shows, included in a catheter (1), a gastrointestinal probe (2) comprising a sensor (3) made of a sensitive material (4) connected to electrical or optical readout means or measurement means.

Said sensitive material (4) undergoes an irreversible change when it is submitted to the cumulative action of the external medium and said irreversible change is measured and recorded by the electrical or optical readout means or measurement means (10). These means (10) can be internal or external to the catheter (1) (see FIG. 1) or maybe absent if measurements are performed only before and after exposure to aggressive forces.

It is a preferred embodiment of the present invention that said sensitive material is part of a matrix composed of one or more electrically conducting composite acid degrading material(s). According to a preferred embodiment of the invention, the matrix comprises as polymeric material, a poly-2-vinylpyridine polymer, copolymerized with styrene or butylmethacrylate and possibly mixed with polymethylmethacrylate, and as electrically conductive material, carbon powder. Another preferred embodiment include 4-vinyl pyridine based polymers.

Any other type of polymer which is subjected to increasing degradation when the acidity increases may be used. For instance, the so-called "controlled drug release coatings" used for "slow release" pharmaceutical products which undergo degradation in acidic media may be used. Specific embodiments of polymers are:

Alternative 1
- 1.00 g. poly(2-vinylpyridine-co-styrene) (Aldrich, granular, styrene content 30%)
- 0.28 g. carbon (325 mesh)
- 6,00 ml dimethylacetamide Alternative 2
- 6.2 g. of a polymer solution consisting of 2% (w/w) poly (2-vinylpyridine-co-styrene) in benzylalcohol
- 4.3 g. carbon (325 mesh)

Alternative 2 is used in a screen printing production process including a thermal treatment (1 hour at 150° C.) after the screen printing step to evaporate the solvent (benzylalcohol) out of said matrix composite.

Screen Printing

The production process comprise the following 30 steps:
- deposit of conducting patterns (Pt, Ag, Pd/Ag, AU) on a substrate (96% $Al_2O_3$),
- deposit of a first dielectricum,
- deposit of a second dielectricum,
- deposit of the sensitive material.

Other possible alternatives include the use of 2-vinylpiridine with 10% styrene or cross-linked with butyl methacrylate 10% instead of poly (2-vinylpyridine).

Figure 2:
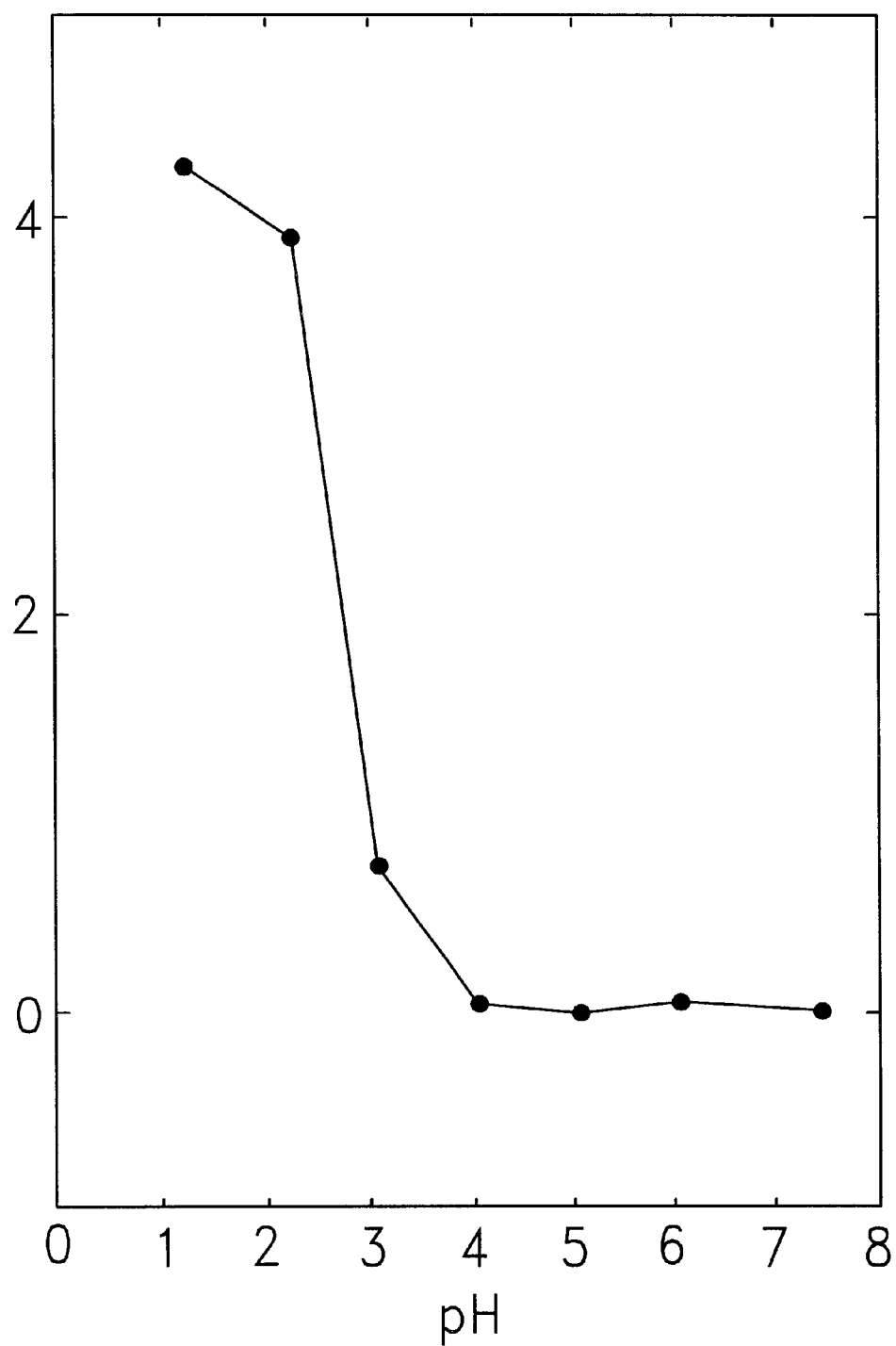

FIG. 2 illustrates the sensor response using said alternative, versus pH of a medium. When measured after a well defined and preset exposure time, as would be the standard procedure in a situation for clinical diagnosis, the sensor response measured in a reference solution (e.g. 0.9% NaCl-solution or in preference a pH buffer solution) shows the pH dependence as in FIG. 2 showing a pronounced response in the pH range below pH 4 which is known to be pathologically significant, and a minimal change in response for higher pH values.

Figure 3A:
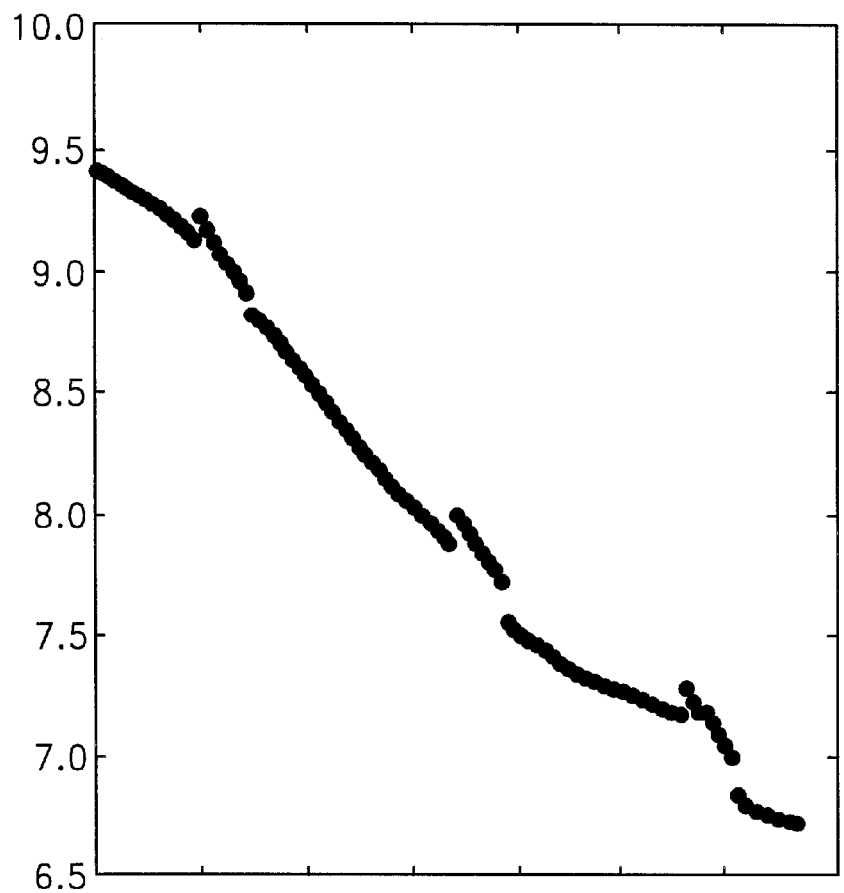
In FIG. 3a, the sensor response, shown as output voltage of the interface circuit in V, is given.
Figure 3B:
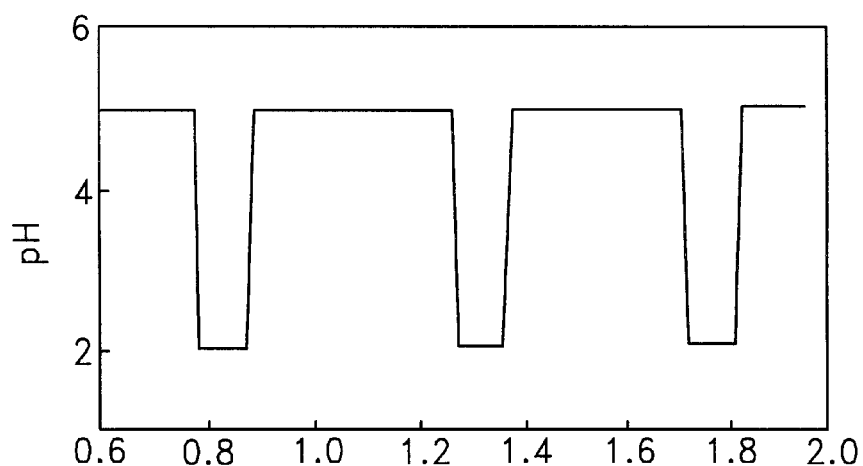
In FIG. 3b, the pH of the solution in which the probe is immersed is given. The FIG. 3a clearly indicates.
Figure 4A:
Figure 4B:
Figure 4C:
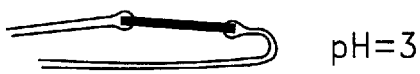
Figure 4D:
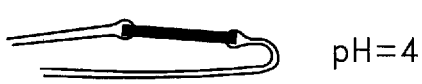
Figure 4E:
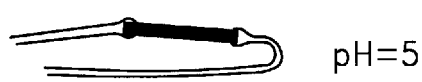

FIGS. 3a and 3b illustrate the cumulative nature of said sensor response (S.R.) and said irreversible changes.

The cumulative nature of the sensor response (S.R.) is best understood when FIGS. 3a and 3b are considered. In these figures, the sensor response (given as a voltage proportional to the conductivity of the sensor) of the state of the art sensor (3b) and of the sensor according to the present invention (3a) is plotted versus the immersion time of the sensors in solutions of various pH. The pH of the solution is depicted in FIG. 3b. As can be seen from the combined pictures, the response of the invented probe is very different from the response of a pH electrode (FIG. 3b) which is known to be used in a variety of state of the art monitoring application in the gastrointestinal tract. It is clearly shown in FIG. 3a that for the given composition of the sensor material, the sensor response is pH dependent and that the sensor response is faster in the more acid solutions. It is also clearly demonstrated that the sensor response of the invented sensor is cumulative, it is the accumulated effect of the exposure to different acidic environments over time. This is essentially contradictory to the nature of any pH-electrode known in the state of the art. This cumulative effect leads directly to the irreversible nature of the invented probe. This is clearly demonstrated in FIG. 4 where a second form of the invented sensor probe is depicted. FIG. 4 shows five indentical sensors which have been exposed to solutions having different pH values for identical exposure times. It is clearly shown that, below pH 4, the sensor element is gradually diminished in dimension, leading to a change in electrical characteristics of the sensor material.

FIG. 5 shows the sensor response when measured after immersion for 20 minutes in a pH 2 solution compared to a 4×6 minutes immersion in pH 2 solution.

Tests 3 and 4 show the sensor response after an immersion time of 20 minutes in a pH 2 solution.

Test 5 shows the sensor response after repeated shorter (5 minutes) immersion period in said solution. It is evident that reproductive characteristics are obtained showing the cumulative nature of the response of said sensitive material.

Preferably and as represented in FIG. 2, the sensor (3) with a sensitive material (4) comprises a substrate (6) with electrical contacts (7) covered by the sensitive material (4) which is an electrically conducting composite material, and possibly by a surrounding layer (encapsulant) (8) which has a retarding effect upon the irreversible change of the said sensitive material (4).

The electrical contacts (7) are connected through wires (9) to an electrical device (10) which measures and records the irreversible change of the sensitive material (4).

If the electrical device (10) is part of the catheter (1, the measurement can be continuous as represented in FIG. 1 or FIG. 2, but the recording device can be extra corporeal, i.e. remain outside the body.

According to another preferred embodiment, the catheter can be free of any electrical or optical devices when it is introduced in the patient's gastrointestinal tract. In this case, the electrical and/or optical devices are connected to the probe only when the probe is removed from the tract in order to measure and record the irreversible change of the sensitive material (4).

According to another preferred embodiment represented in FIG. 7, the gastrointestinal probe may also consist of an optical fibre based system (11), wherein a cladding portion of said optical fibre (13) is removed and replaced by a sensor (3) having the sensitive material (4) as above described.

Said sensitive material (4) undergoes an irreversible change when it is submitted to the cumulative action of the external medium and said irreversible change is measured and recorded, possibly continuously, by an optical device (not represented).

If the gastrointestinal probe is to be monitored by means of optical techniques, it might be advantageous to limit the composition of the sensitive material (4) and avoid the inclusion of any electrically conductive material.

Said irreversible change may consist of modification of refractive index, light absorption of or any other optical property of said material when it is submitted to the cumulative action of the external medium.

The form and the size of the gastrointestinal probe according to the invention or its catheter can differ according to the specific application or introduction pathways into the gastrointestinal tract.

What is claimed is:

1. A gastrointestinal probe comprising a sensitive material connected to a sensor portion adapted to be connected to a readout or measurement device, the sensitive material being a polymeric material and undergoing an irreversible change when submitted to a cumulative action of an external medium so that the sensor portion senses the irreversible change and transmits information indicative of the irreversible change to the readout or measurement device for recording or measurement thereof.

2. A gastrointestinal probe as defined in claim 1, wherein the information transmitted to the readout or measurement device is in electrical or optical form.

3. A gastrointestinal probe as defined in claim 1, wherein the irreversible change of said sensitive material is selected from the group consisting of swelling, hydrolysis, molecular modifications, decrease in mass, etching, decomposition, modification of refractive index, light absorption of said sensitive material.

4. A gastrointestinal probe as defined in claim 1, wherein the polymeric material is at least one selected from the group consisting of pyridine, styrene, methacrylate based polymers and copolymers, acid resistant polymers, polymeric compositions used as drug coating for pH dependent delivery of active compounds or a mixture thereof.

5. A gastrointestinal probe as defined in claim 1, wherein the sensor portion comprises an electrically conducting material or a matrix of electrically conductive materials.

6. A gastrointestinal probe as defined in claim 5, wherein the electrically conductive materials are elements selected from the group consisting of metals, semi-conducting oxides, carbon, electronically conducting polymers or a mixture thereof.

7. A gastrointestinal probe as defined in claim 1, wherein the sensitive material is covered with a layer having a retarding effect on the irreversible change of the sensitive material.

8. A gastrointestinal probe as defined in claim 1, wherein the sensor portion comprises a substrate patterned with an electrically conductive material.

9. A process for making a gastrointestinal probe as defined in claim 8, comprising:

providing a sensor portion by microelectronic patterning a substrate; and depositing the sensitive material upon at least one portion of the patterned substrate.

10. A process as defined in claim 9, wherein the microelectronic patterning the substrate photolithographic patterning of a substrate followed by evaporation, sputtering, plating and/or deposition of a metallic or conductor pattern and insulation layers.

11. A process a defined in claim 9, wherein the microelectronic patterning the substrate comprises screen printing of metallic conductor and insulator patterns on an inert substrate, preferably chosen among the group consisting of alumina, oxidized silicon, flexible polymer substrates and/or a mixture thereof.

12. A gastrointestinal probe as defined in claim 1, wherein the sensor portion comprises an optical fiber.

13. A gastrointestinal probe as defined in claim 12, wherein the optical fiber has a core and a claddidng enclosing the core, a part of the cladding of the optical fiber being replaced with a sensitive material.

14. A gastrointestinal probe as defined in claim 12, wherein the irreversible change of the sensitive material is optically detected and transmitted to the readout or measurement device.

15. A process for making a gastrointestinal probe as defined in claim 12, comprising;

providing an optical fiber having a core and a cladding enclosing the core;

removing a part of the claddidng of the optical fiber to expose a part of the core; and covering the exposed part of the core with the sensitive material.

16. A method of measurement, comprising the step of using the gastrointestinal probe as defined in claim 1 in a gastrointestinal tract or after removal therefrom.

17. A method of measurement, comprising the step of inserting the gastrointestinal probe as defined in claim 1 into a gastrointestinal tract of a patient.

\* \* \* \* \*